(12) United States Patent
Yung et al.

(10) Patent No.: US 9,109,203 B2
(45) Date of Patent: Aug. 18, 2015

(54) METHOD OF EXTRACTING NEURAL STEM CELLS USING NANOPARTICLES

(71) Applicant: Hong Kong Baptist University, Kowloon (HK)

(72) Inventors: Kin-Lam Yung, Kowloon (HK); Hung-Wing Li, Kowloon (HK); Nga-Ping Lui, Kowloon (HK); Yat-Ping Tsui, Kowloon (HK); See-Lok Ho, Kowloon (HK); Ying-Shing Chan, Kowloon (HK); Kwok-Yan Shum, Kowloon (HK); Edman Shik-Chi Tsang, Kowloon (HK)

(73) Assignee: HONG KONG BAPTIST UNIVERSITY, Kowloon Tong, Kowloon (HK)

( * ) Notice: Subject to any disclaimer, the term of this patent is extended or adjusted under 35 U.S.C. 154(b) by 0 days.

(21) Appl. No.: 13/834,750

(22) Filed: Mar. 15, 2013

(65) Prior Publication Data

US 2014/0134698 A1  May 15, 2014

Related U.S. Application Data

(60) Provisional application No. 61/726,762, filed on Nov. 15, 2012.

(51) Int. Cl.
*C12N 13/00* (2006.01)
*C12N 5/079* (2010.01)
*C12N 5/0797* (2010.01)

(52) U.S. Cl.
CPC .................... *C12N 5/0623* (2013.01)

(58) Field of Classification Search
None
See application file for complete search history.

(56) References Cited

U.S. PATENT DOCUMENTS 7,309,316 B1 * 12/2007 Flynn et al. ................. 600/562

OTHER PUBLICATIONS

Hofstetter et al., Allodynia limits the usefulness of intraspinal neural stem cell grafts; directed differentiation improves outcome, Nature Neuroscience, vol. 8 No. 3, Mar. 2005.
Lu et al., Bifunctional Magnetic Silica Nanoparticles for Highly Efficient Human Stem Cell Labeling, Nano Letters, vol. 7, No. 1, 2007.
Cho et al., A magnetic switch for the control of cell death signalling in in vitro and in vivo systems, Nature Materials, vol. 11, Dec. 2012, www.Nature.com/Naturematerials.
Moreno-Manzano et al., Activated Spinal Cord Ependymal Stem Cells Rescue Neurological Function, Stem Cells, 27:733-743, 2009, www.Stemcells.com.
Chiasson et al., Adult Mammalian Forebrain Ependymal and Subependymal Cells Demonstrate Proliferative Potential, but only Subependymal Cells Have Neural Stem Cell Characteristics, The Journal of Neuroscience, 19 (11):4462-4471, Jun. 1, 1999.
Fuentealba et al., Adult Neural Stem Cells Bridge Their Niche, Cell Stem Cell 10, Jun. 4, 2012, ©2012 Elsevier Inc.
Ming & Song, Adult Neurogenesis in the Mammalian Brain: Significant Answers and Significant Questions, Neuron 70, May 26, 2011, © 2011 Elsevier Inc.
Teng et al., Functional recovery following traumatic spinal cord injury mediated by a unique polymer scaffold seeded with neural stem cells, PNAS, vol. 99 No. 5, 3024-3029, Mar. 5, 2002.
Coskun et al., CD133+ neural stem cells in the ependyma of mammalian postnatal forebrain, PNAS, vol. 105 No. 3, 1026-1031, Jan. 22, 2008.
Sim et al., CD140a identifies a population of highly myelinogenic, migration-competent, and efficiently engrafting human oligodendrocyte progenitor cells, Nat Biotechnol., 29(10): 934-941. doi:10.1038/nbt.,1972.
Lee et al., Divalent metal transporter, iron, and Parkinson's disease: A pathological relationship, Cell Research (2010), 20:397-399, doi: 10.1038/cr.2010.39, published online Apr. 1, 2010.
Yu et al., Drug-Loaded Superparamagnetic Iron Oxide Nanoparticles for Combined Cancer Imaging and Therapy in Vivo, Angew. Chem. Int. Ed., 47, 5362-5365, 2008.
Lee et al., Exchange-coupled magnetic nanoparticles for efficient heat induction, Nature Nanotechnology, vol. 6, Jul. 2011.
Carlen et al., Forebrain ependymal cells are Notch-dependent and generate neuroblasts and astrocytes after stroke, Nature Neuroscience, vol. 12 No. 3, Mar. 2009.
Takahashi & Yamanaka, Induction of Pluripotent Stem Cells from Mouse Embryonic and Adult Fibroblast Cultures by Defined Factors, Cell 26, 663-676, Aug. 25, 2006, © 2006 Elsevier Inc.
Pluchino et al., Injection of adult neurospheres induces recovery in a chronic model of multiple sclerosis, Nature, vol. 422, Apr. 17, 2003, www.nature.com/nature.
Zecca et al., Iron, Brain Ageing and Neurodegenerative Disorders, Nature Reviews Neuroscience, vol. 5, Nov. 2004.
Richardson et al., Grafts of adult subependymal zone neuronal progenitor cells rescue hemiparkinsonian behavioral decline, Brain Research 1032,11-22, (2005).
Wagner et al., Heme and Iron Metabolism: Role in Cerebral Hemorrhage, Journal of Cerebral Blood Flow & Metabolism, 23:629-652, 2003, © The International Society for Cerebral Blood Flow and Metabolism Published by Lippincott Williams & Wilkins, Inc., Baltimore.
Gould, How widespread is adult neurogenesis in mammals?, Nature Reviews Neuroscience, vol. 8, Jun. 2007.
McBride et al., Human Neural Stem Cell Transplants Improve Motor Function in a Rat Model of Huntington's Disease, The Journal of Comparative Neurology, 475:211-219, (2004).
Johansson et al., Identification of a Neural Stem Cell in the Adult Mammalian Central Nervous System, Cell, vol. 96, 25-34, Jan. 8, 1999, Copyright 1999 by Cell Press.

(Continued)

*Primary Examiner* — Blaine Lankford
*Assistant Examiner* — David Berke-Schlessel
(74) *Attorney, Agent, or Firm* — Ella Cheong Hong Kong; Sam T. Yip

(57) ABSTRACT

A method of extracting neural stem cells from a living subject, comprising the steps of introducing magnetic nanoparticles into the subject, targeting the neural stem cells with the magnetic nanoparticles to form magnetic nanoparticle-targeted cells, isolating the magnetic nanoparticle-targeted cells, extracting the magnetic nanoparticles-targeted cells from the subject.

21 Claims, 15 Drawing Sheets

(56) References Cited

OTHER PUBLICATIONS

Chojnacki et al., Identity crisis for adult periventricular neural stem cells: subventricular zone astrocytes, ependymal cells or both?, Nature Reviews Neuroscience, vol. 10, Feb. 2009.

Zhao et al., Notch keeps ependymal cells in line, Nature Neuroscience, vol. 12 No. 3, Mar. 2009.

Bogart et al., Photothermal Microscopy of the Core of Dextran-Coated Iron Oxide Nanoparticles During Cell Uptake, ACS Nano, vol. 6 No. 7, 5961-5971, 2012.

Vogel, Ready or Not? Human ES Cells Head Toward the Clinic, Science, vol. 308, Jun. 10, 2005, www.sciencemag.org Published by AAAS.

Saadi et al., Layer-by-Layer Electrostatic Entrapment of Protein Molecules on Superparamagnetic Nanoparticle: A New Strategy to Enhance Adsorption Capacity and Maintain Biological Activity, J. Phys. Chem., 113, 15260-15265, C 2009.

Sun et al., Magnetic Nanoparticles in MR Imaging and Drug Delivery, Adv Drug Deliv Rev.; 60(11): 1252-1265, doi:10.1016/j.addr. 2008.03.018, Aug. 17, 2008.

Vatta et al., Magnetic nanoparticles: Properties and potential applications, Pure Appl. Chem., vol. 78, No. 9, pp. 1793-1801, 2006.

Windrem et al., Neonatal chimerization with human glial progenitor cells can both remyelinate and rescue the otherwise lethally hypomyelinated shiverer mouse, Cell Stem Cell.; 2(6): 553-565. doi:10.1016/j.stem.2008.03.020., Jun. 5, 2008.

Pluchino et al., Neurosphere-derived multipotent precursors promote neuroprotection by an immunomodulatory mechanism, Nature, vol. 436, Jul. 14, 2005 doi:10.1038/nature03889.

Weinstein et al., Superparamagnetic iron oxide nanoparticles: diagnostic magnetic resonance imaging and potential therapeutic applications in neurooncology and central nervous system inflammatory pathologies, a review, Journal of cerebral Blood Flow & Metabolism 30, 15-35, (2010).

Lin & Haynes, Synthesis and Characterization of Biocompatible and Size-Tunable Multifunctional Porous Silica Nanoparticles, Chem. Mater., 21, 3979-3986, 2009.

Boyer et al., The design and utility of polymer-stabilized iron-oxide nanoparticles for nanomedicine applications, NPG Asia Materials, 2(1) 23-30, Jan. 2, 2010, www.natureasia.com/asia-materials.

Miura et al., Variation in the safety of induced pluripotent stem cell lines, Nature Biotechnology advance online publication, 1-3, published online Jul. 9, 2009; doi:10.1038/nbt.1554.

Doetsch et al., Subventricular Zone Astrocytes Are Neural Stem Cells in the Adult Mammalian Brain, Cell, vol. 97, 703-716, Jun. 11, 1999, Copyright © 1999 by Cell Press.

\* cited by examiner

METHOD OF EXTRACTING NEURAL STEM CELLS USING NANOPARTICLES

CROSS-REFERENCE TO RELATED APPLICATIONS

The present application claims priority of U.S. provisional application No. 61/726,762 filed Nov. 15, 2012, content of which being incorporated by reference in its entirety.

FIELD OF INVENTION

This invention relates to a method of extracting biological cells from a subject, particularly, but not exclusively, a method of extracting neural stem cells from a living subject.

BACKGROUND OF INVENTION

One grand challenge in neural stem cell research and regenerative medicine is the precise isolation and extraction of functional neural stem cells from adult brains. Neural stem cells (NSCs) are self-renewing and multipotent in nature, allowing cell replacement therapies for diseases in the nervous system, which are generally incurable at present. Currently, neural stem cells can only be obtained from foetal tissues or differentiated from other cell types as alternative sources. At present it is practically impossible to obtain neural stem cells directly from the patients themselves who are often adults. The objective of the present invention is to provide a method for extracting biological cells, particularly neural stem cells from a subject in which the aforesaid shortcomings are mitigated or at least to provide a useful alternative.

SUMMARY OF INVENTION

Accordingly, there is provided a method of extracting biological cells from a subject. The method comprises introducing magnetic nanoparticles into the subject, targeting biological cells with the magnetic nanoparticles to form magnetic nanoparticle-targeted cells, isolating the magnetic nanoparticle-targeted cells, and extracting the magnetic nanoparticles-targeted cells from the subject.

Preferably, the step of targeting further comprises a step of incubating the biological cells with the magnetic nanoparticles.

Preferably, the step of isolating further comprises a step of agitating the magnetic nanoparticle-targeted cells.

Preferably, the step of agitating comprises using of magnetic force.

Preferably, the magnetic force is applied external to the subject.

Preferably, the magnetic nanoparticles are coated with silica.

Preferably, the magnetic nanoparticles are surface conjugated with cell markers.

Preferably, the magnetic nanoparticles are fluorescent.

Preferably, the cell markers comprise stem cells surface markers.

Preferably, the stem cells surface markers comprise antibodies CD133.

Preferably, the biological cells are neural stem cells.

Preferably, the method is performed at a subventricular zone of a brain of the subject.

Preferably, the magnetic nanoparticles are superparamagnetic.

Preferably, the magnetic nanoparticles are made from materials selected from a group consisting of iron oxide, maghemite ($Fe_2O_3$), magnetite ($Fe_3O_4$) nanoparticles, and a mixture thereof.

Preferably, the step of introducing comprises a step of injecting.

Preferably, the subject is a living organism.

Preferably, the subject comprises juvenile or adult human.

Preferably, the step of incubating lasts for less than or equal to about 24 hour.

Preferably, the step of incubating lasts for about 6 hour.

Preferably, the step of agitating lasts for less than or equal to about 15 min

Preferably, the magnetic force is applied via a rotational magnetic field.

Preferably, the step of extracting comprises using of tools selected from the group of a syringe, a magnet probe, a neodymium magnet and a mixture thereof.

Preferably, the method is applied in vitro.

Preferably, the method is applied in vivo.

Preferably, the method is used for treating, preventing or delaying progression of a neural related disease of a patient.

Preferably, the patient comprises juvenile or adult human.

Preferably, the method is used in tailor-made cell replacement therapy using the patient's own neural stem cells for transplantation and treatment of the neural related diseases.

Preferably, the method is employed for identifying neural stem cells population for targeted neural stem cells extraction.

BRIEF DESCRIPTION OF DRAWINGS

The present invention will become apparent from the following description, when taken in conjunction with the accompanying drawings, in which.

DETAILED DESCRIPTION OF THE INVENTION

The present invention relates to a nano-particle based extraction system for the collection of $CD133^+$ ependymal cells from adult mammals. $CD133^+$ ependymal cells are neural stem cells which exist in a relatively large amount in a brain structure called choroid plexus, which lines along the subventricular zone (SVZ) of the brain. Subventricular zone is hollow in nature, which allows surgical extractions of cells in vivo without causing major brain damages. Magnetic nanoparticles (MNPs) comprise iron oxide, maghemite ($Fe_2O_3$) magnetite ($Fe_3O_4$) or a mixture thereof with an encapsulation of a protective hydrophilic silica shell, are employed as biocompatible nano-devices for cell trapping. Preferably, the nanoparticles are superparamagnetic. To enhance the specificity of the cell extraction, anti-CD133 antibodies (CD133 is a cell surface marker for identifying the stem cell population) have been conjugated to MNPs.

The antibodies conjugated MNPs (Ab-MNPs) are introduced by injection into the SVZ of a subject and incubated for few hours to allow targeting of the Ab-MNPs with the neural stem cells (NSCs). The subject will be subjected to a spinning process to facilitate the isolation of the targeted cells, in which the subject will be placed within a magnetic field to facilitate detachment of the target cells, with the magnetic field applied external to the subject. Preferably, the magnetic field is a rotation magnetic field. The detached cells will be extracted and collected by either with the syringe or a neodymium magnet probe for further culture. The subjects are found to be able to survive after the extraction process.

The extracted cells are then cultured in neurosphere-promoting conditions. The neurospheres are subsequently collected for the differentiation of the cells of interest, such as neurons.

Synthesis and Validation of MNPs

Figure 1:
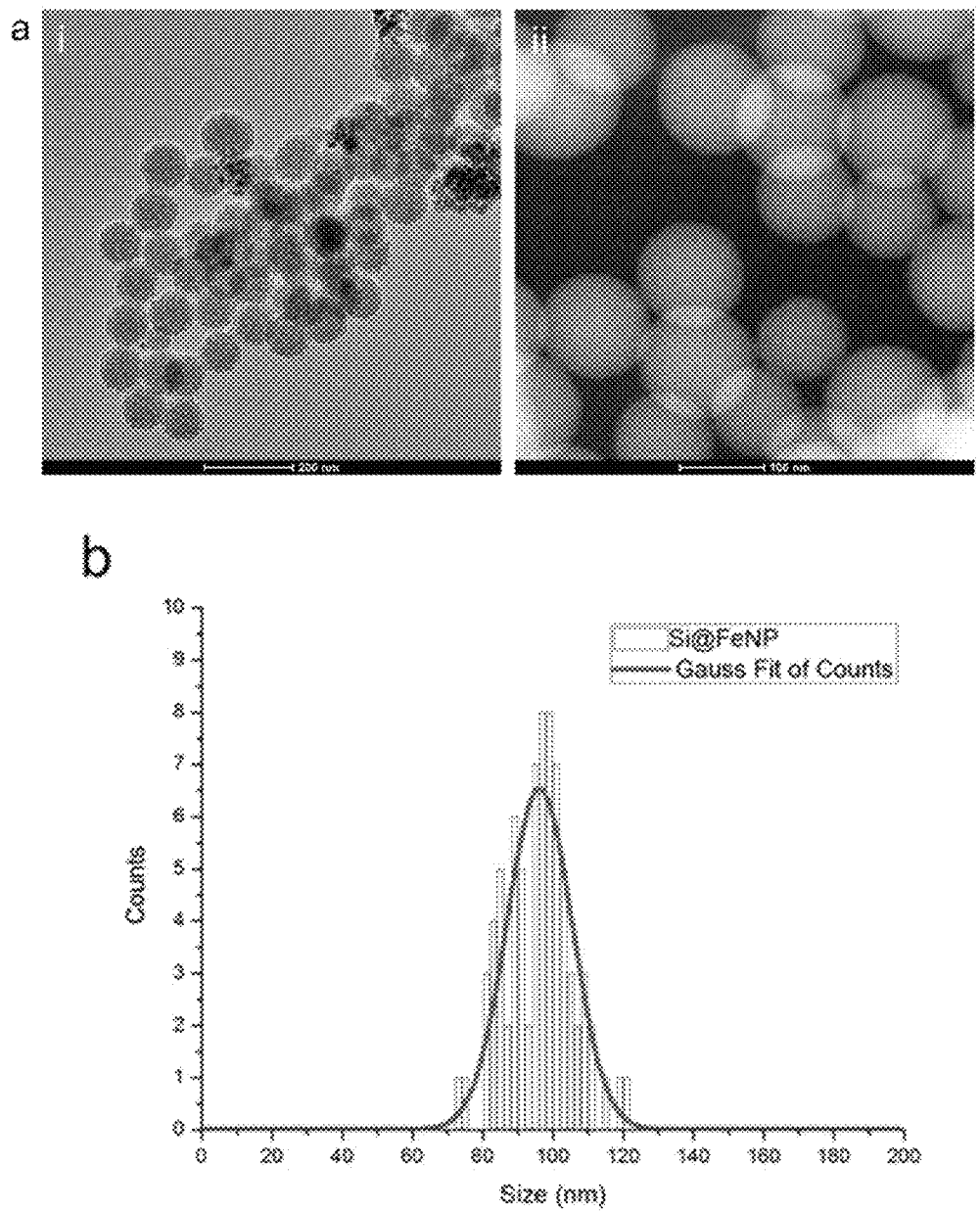
FIG. 1(a) shows the Transmission electron micrographs of typical MNPs coated with silica, with a size of the particle of approximately 100 nm in diameter.
FIG. 1(b) shows the size distribution of the silica-coated MNP's with average size of 97±13 nm.

The synthesis of the MNPs, coating of the MNPs with silica and then fluorescence, and the subsequent conjugation of antibodies CD133 onto the fluorescent silica coated Ab-MNPs are synthesized according to the methods described in the Methodology section below. As seen from FIG. 1, the MNPs are found to show narrow particle size distribution, with the size of the particles being approximately 100 nm in diameter as revealed by the transmission electron micrography (TEM) (FIG. 1a, scale bar: (A,i) 200 μm; (A,ii) 100 μm), and an average size of 97±13 nm as revealed by the size distribution (FIG. 1b).

Figure 2:
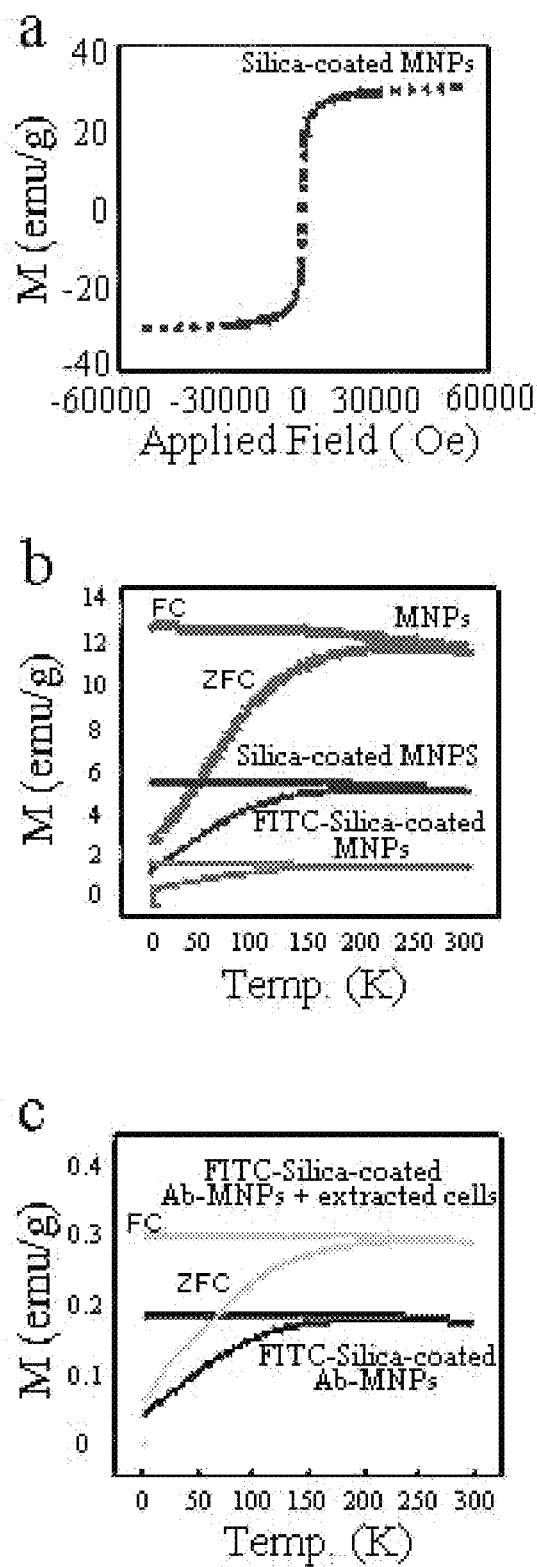
FIG. 2(a) shows a saturation magnetisation curve of iron oxide in silica.
FIG. 2(b) shows the magnetic susceptibility per gram of the MNP's as a function of temperature (5 to 300 K) for the zero-field-cooled (ZFC) conditions of the specimens.
FIG. 2(c) shows the magnetic susceptibility per gram of the MNP's as a function of temperature (5 to 300 K) for field cooled (FC) conditions of the specimens.

The magnetic susceptibility of these particles was also measured and optimized. As shown in FIG. 2, a saturation magnetisation curve of typical iron oxide nanoparticles coated with silica in an increasing magnetic field was first measured. This was followed by probing magnetic susceptibility curves of all functional iron oxide particles by superconducting quantum interference device (SQUID) with and without an external magnetic weak field of 100 Orested (Oe) (FIGS. 2b and 2c). It is noted that a high saturation magnetisation value was of about 30 emu/g was retained over the silica coated iron oxide particles as compared to 70-80 emu/g of naked iron oxide (FIG. 2a). The FC and ZFC magnetization curves are split at and below blocking temperature (TB is the transformation of ferromagnetism to superparamagnetism). It is thus evident that all the materials clearly exhibit ferromagnetic properties for the whole temperature range (TB above 300 K). As seen from the figure that an increasing quantity of non-ferromagnetic or slightly anti-ferromagnetic coating including silica, antibodies, fluorescent tag and cells (from 13 to 0.2 emug$^{-1}$ under FC conditions) have substantially reduced the susceptibility value of MNPs. Attempted have been made with different sizes of MNPs (20, 50, 100 nm) and found that the larger the size of the synthesized MNPs, the higher is the susceptibility value (not shown). In particular, there was no apparent agglomeration for the 100 nm MNPs with and without the application of external field, presumably the thick silica coatings render magnetic isolation of each MNP (low coercivity). In the application of strong magnetic field the force on the magnetic body is given as F=I (δH/δX)=χ H (δH/δX). F is the force per unit volume on the body in the direction of increasing magnetic field, I is the intensity of magnetisation, χ is the magnetic susceptibility and H is the magnetic field strength, as described in A. Al-Saadi et al., *Layer-by-Layer Electrostatic Entrapment of Protein Molecules on Superparamagnetic Nanoparticle: A New Strategy to Enhance Adsorption Capacity and Maintain Biological Activity. J Phys Chem C* 113, 15260 (Aug. 27, 2009). It has been demonstrated in the text that using a typical home made ~6,000 G NdFeB magnetic probe needle of 2 mm id and 10 mm in length is sufficient to induce magnetic separation of the small ferromagnetic particles. Further optimization of magnetic separation using functional iron oxide in silica is underway.

Figure 3:
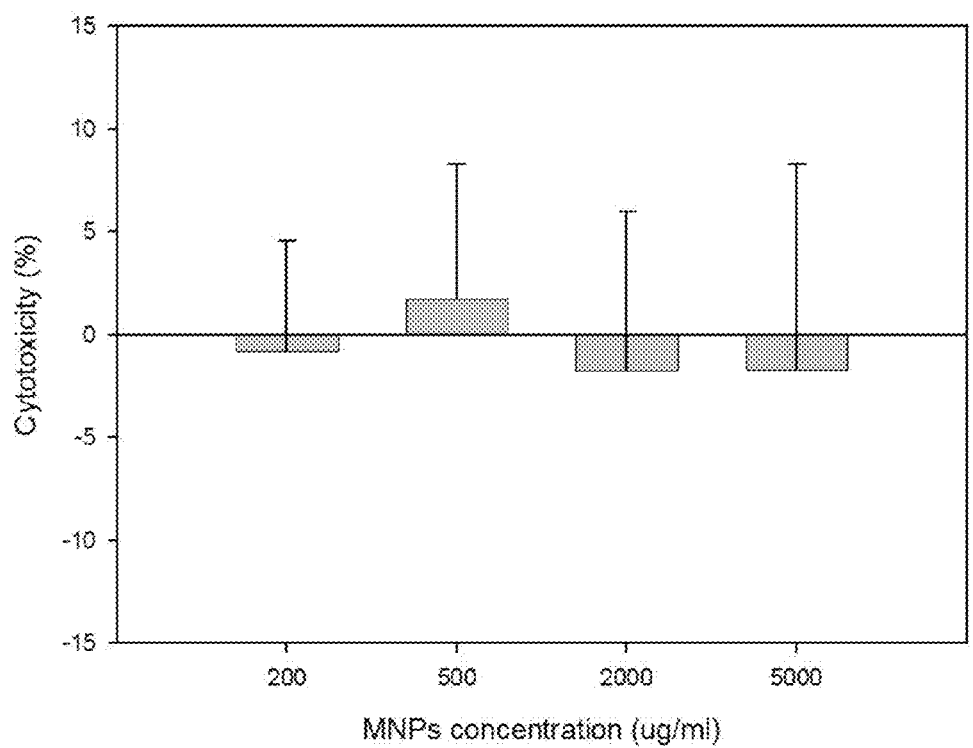
FIG. 3 shows the lactate dehydrogenase (LDH) cytotoxicity assay indicating that the percentage of cell death in P0 rat ventricle after 24-hour treatment with different concentrations of MNPs (200-5000 μg/ml).

Before further processing of these particles, their cytotoxicity was first assessed by lactate dehydrogenase (LDH) cytotoxicity assay. As shown in FIG. 3, the percentage of cell death in P0 rat ventricle after 24-hour treatment with MNPs in the concentration range of 200-5000 μg/ml was comparable with the control indicating that the MNPs were not toxic.

Figure 4:
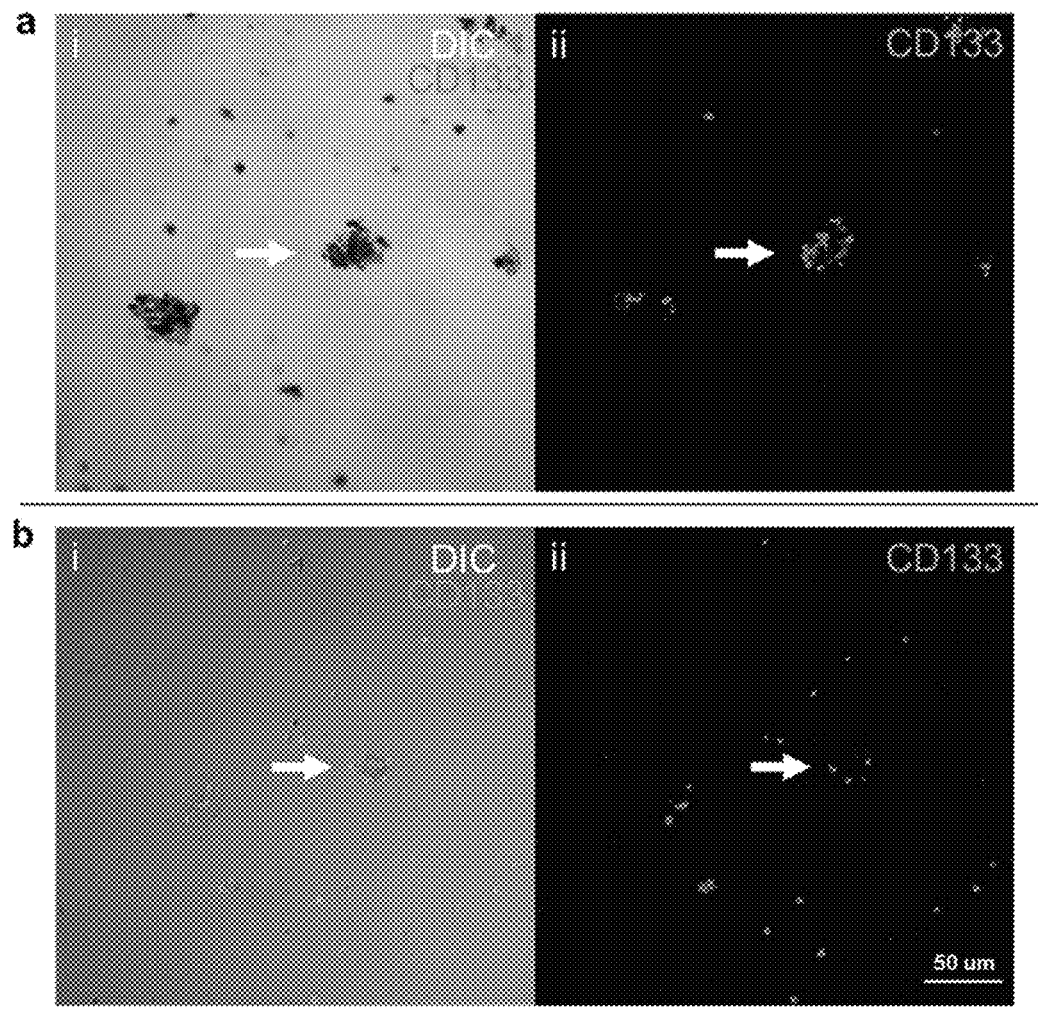
FIG. 4(a) shows the selective isolation of $CD133^+$ astrocytes with FITC conjugated antibodies conjugated MNPs (Ab-MNPs).
FIG. 4(b) shows that the $CD133^-$SH-SY5Y cells do no favor the binding of the FITC conjugated antibodies conjugated MNPs (Ab-MNPs).

Specificity of the Ab-MNPs to NSCs was also assessed. Primary astrocytes (CD133$^+$) and SH-SY5Y (CD133$^-$) were employed for an in vitro test and Ab-MNPs were first fluorescently labeled with FITC (fluorescein isothiocyanate). By merging the differential interference contrast (DIC) and confocal images, the distribution of Ab-MNPs in a cell solution was monitored. It is shown in FIG. 4 that the Ab-MNPs favorably bind to the cell surface of the CD133$^+$ astrocytes. With a magnetic field applied to the cell culture, the CD133$^+$ cells tagged with Ab-MNPs are effectively driven in the solution. While for the SH-SY5Y cell culture, the Ab-MNPs were evenly distributed in the solution but the cells were immobile with the application of a magnetic field.

Figure 5A:
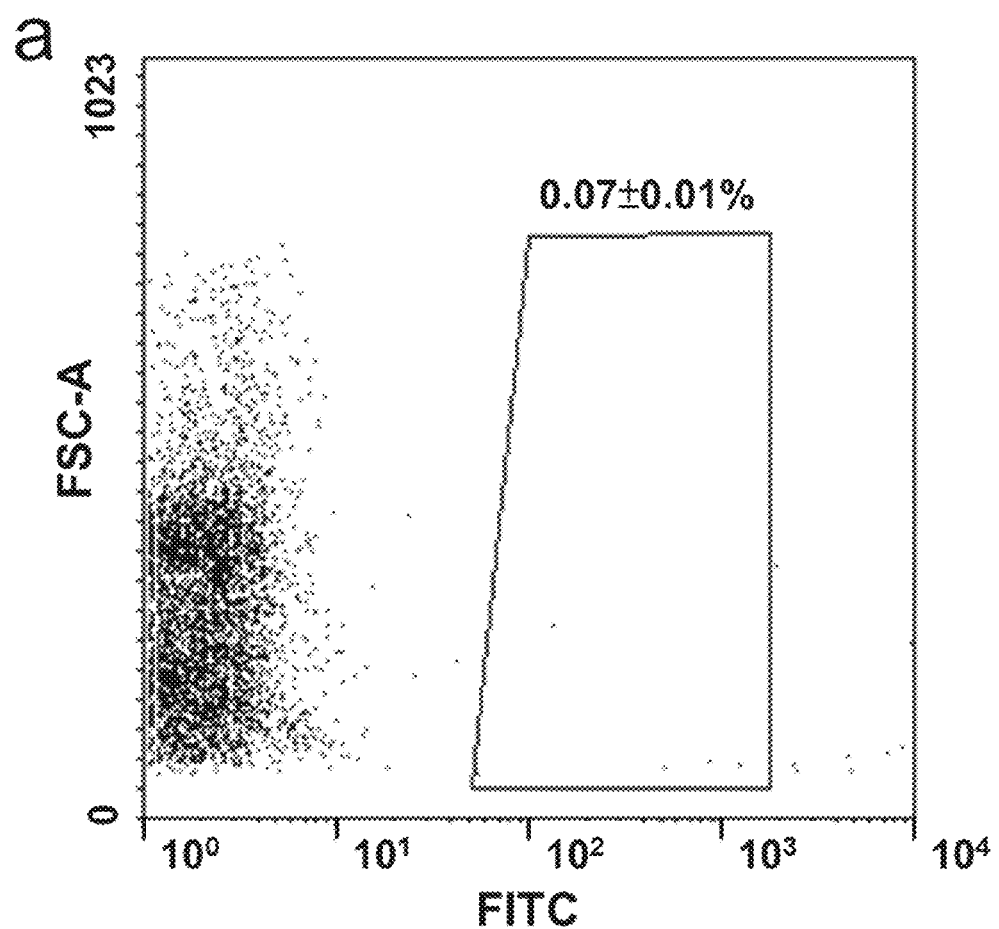
FIG. 5(a) shows the flow cytometry control experiment with no Ab-MNPs.
Figure 5B:
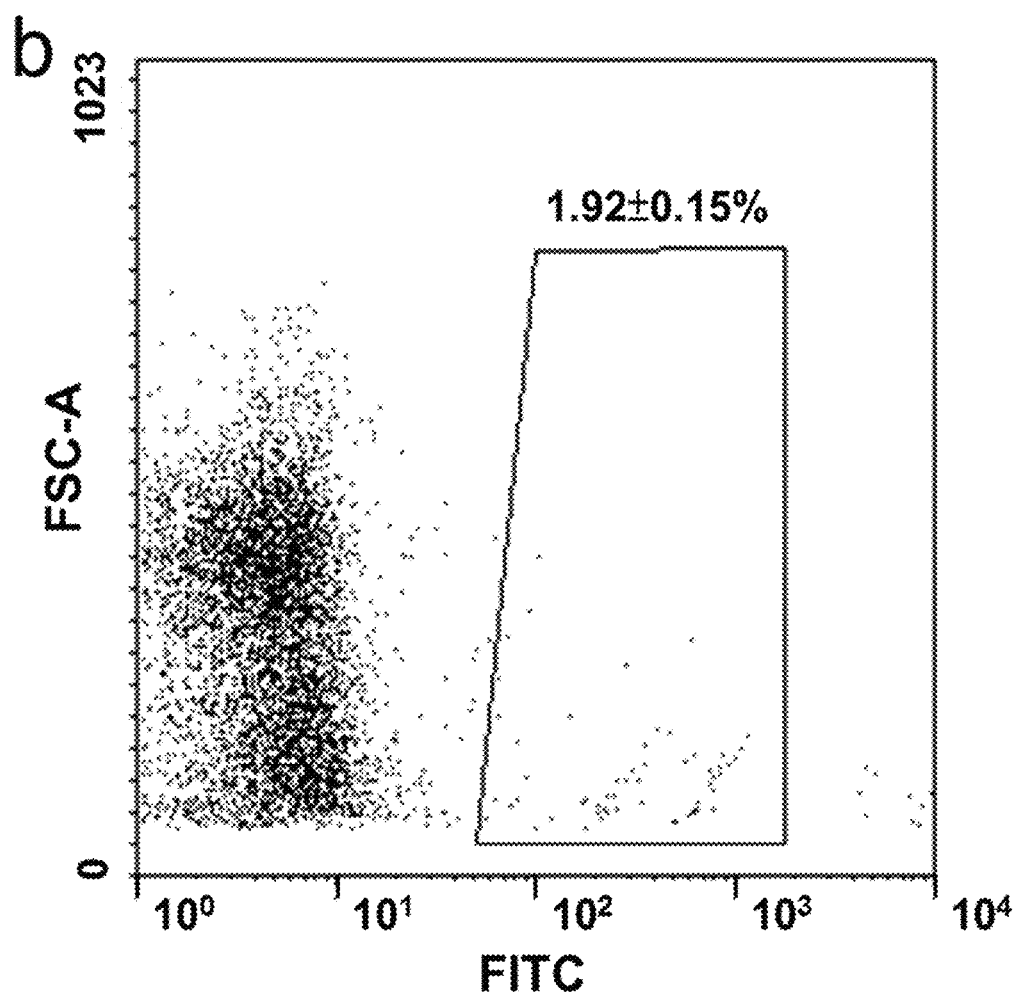
FIG. 5(b) shows the Ab-MNPs incubated ventricular cells without magnetic separation.
Figure 5C:
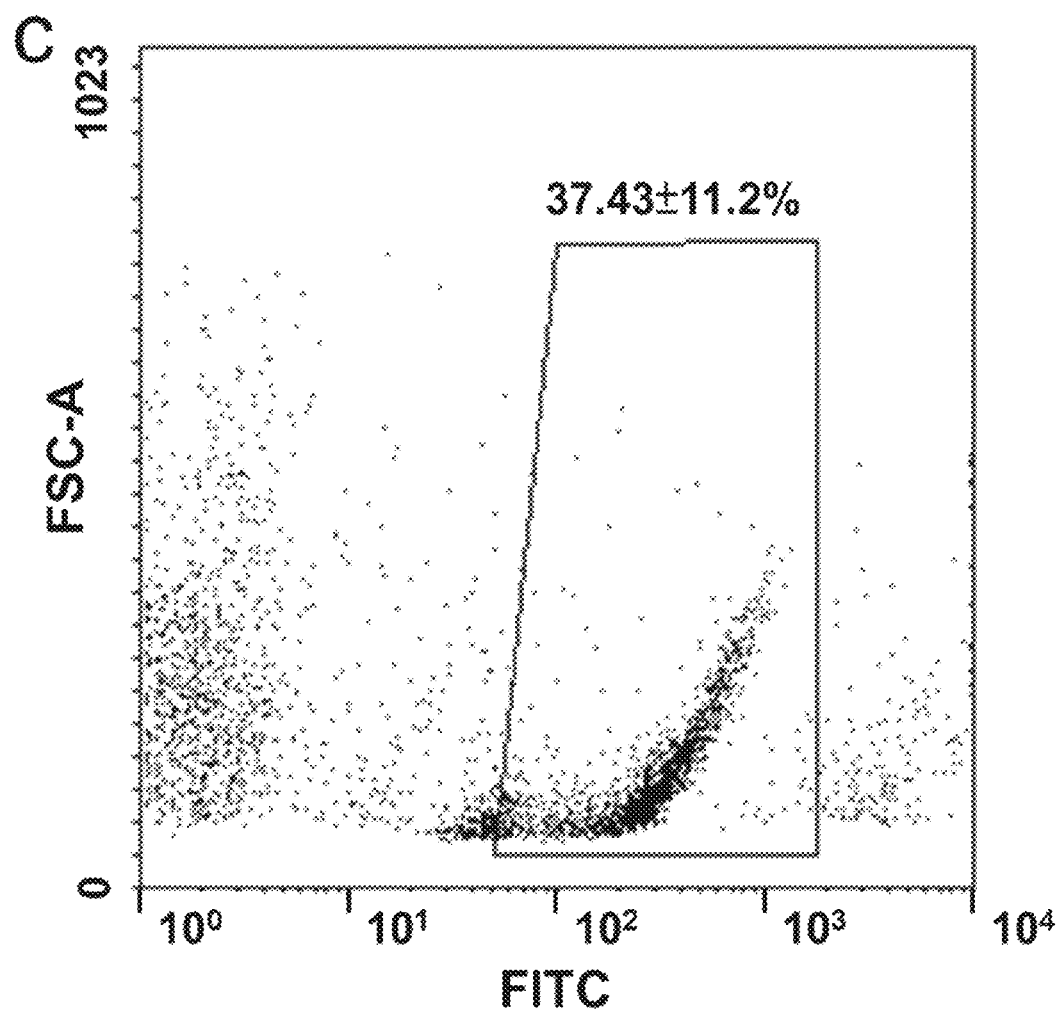
FIG. 5(c) shows the Ab-MNPs incubated ventricular cells after the magnetic separation treatment.
Figure 5D:
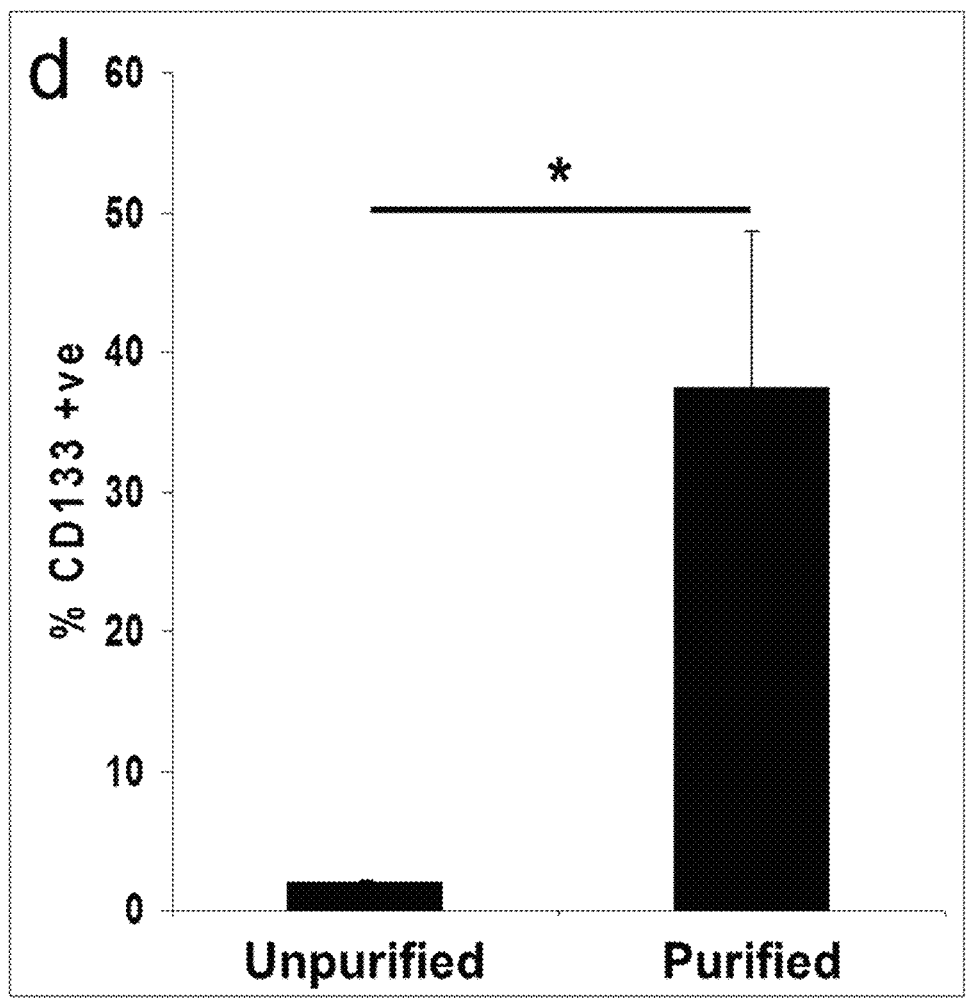
FIG. 5(d) shows that 37.43±11.2% of collected cells in solution were CD133 positive after the magnetic separation treatment.
Figure 5E:
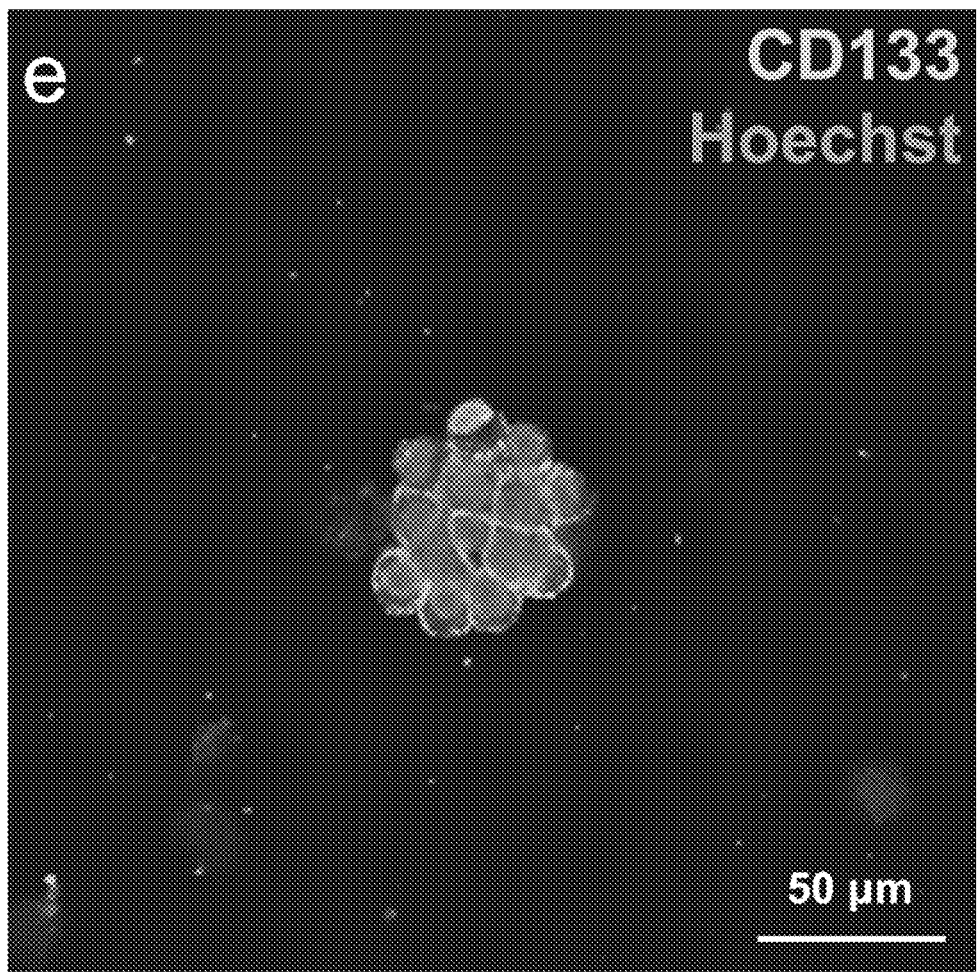
FIG. 5(e) shows that the results of the immunocytochemistry which revealed CD133 expression of the purified ventricular cells.

The Ab-MNPs were then tested for their ability to recognize and extract CD133$^+$ NSCs in vitro by magnetic means by a flow cytometry analysis. As shown in FIG. 5, a flow cytometry analysis of the Ab-MNPs incubated lateral ventricle cells dissociated without magnetic separation treatment revealed that only 1.92±0.15% of the cells were CD133$^+$ in solution phase (FIG. 5b). After magnetic separation the percentage of CD133$^+$ cells increased to 37.43±11.2% (FIG. 5c) from 1.92±0.15% which was gained by almost 20 folds in the solution concentration (FIG. 5(d)). Immunocytochemistry was also performed to visualize the CD133$^+$ expression of purified cells (FIG. 5e). The results indicated that Ab-MNPs can be used to recognize and further magnetically purify or extract CD133$^k$ neural stem cells through simple magnetic means.

Targeting NSCs in the SVZ of Adult SD Rats

Figure 6:
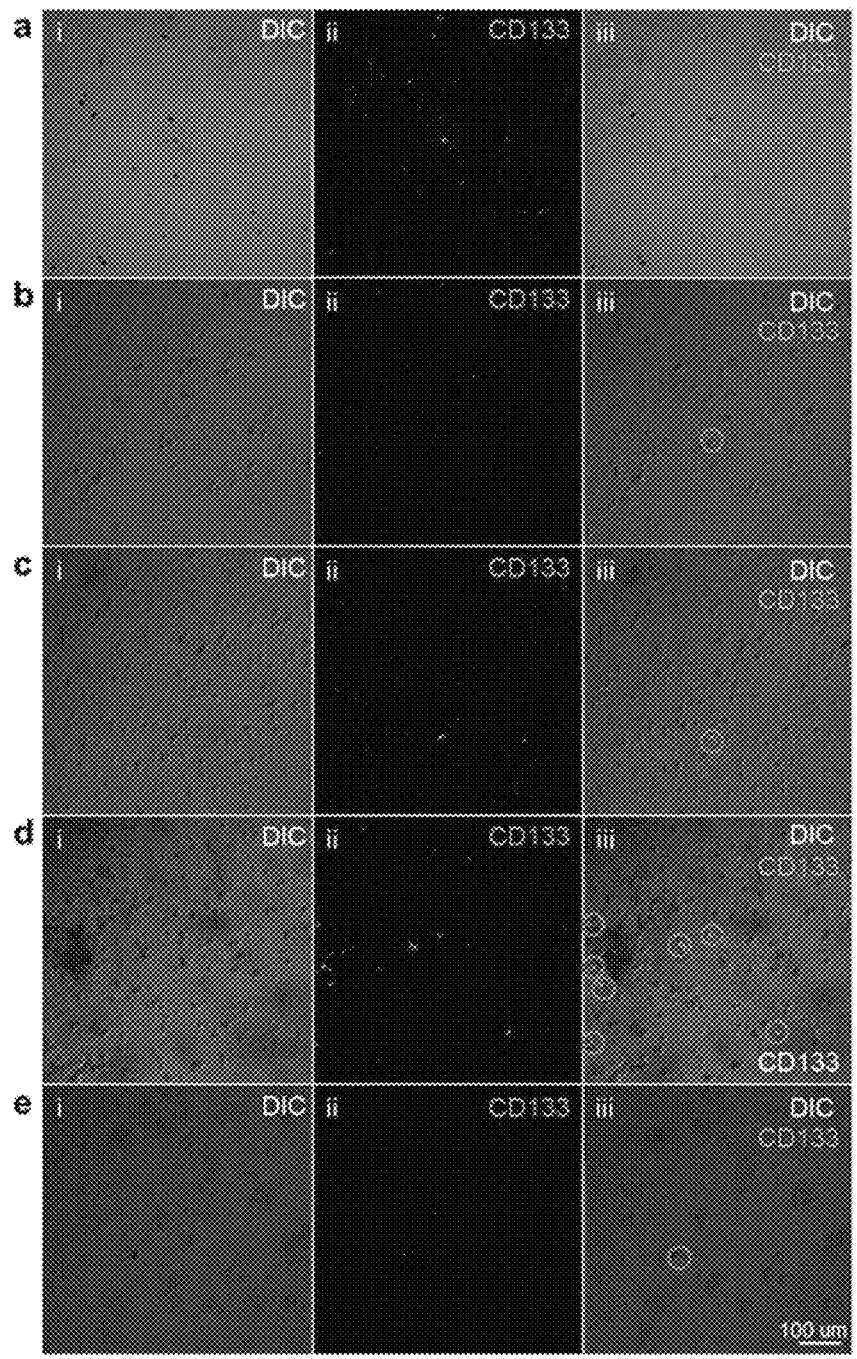
FIG. 6(a) shows a study of optimal incubation time for efficient extraction of NSCs from SVZ of 0-hours with Ab-MNP's (2000 μg/ml in 5 μl of PBS) applied in vivo with corresponding images captured from the extract.
FIG. 6(b) shows a study of optimal incubation time for efficient extraction of NSCs from SVZ of 1-hour with Ab-MNP's (2000 μg/ml in 5 μl of PBS) applied in vivo with corresponding images captured from the extract.
FIG. 6(c) shows a study of optimal incubation time for efficient extraction of NSCs from SVZ of 3-hours with Ab-MNP's (2000 μg/ml in 5 μl of PBS) applied in vivo with corresponding images captured from the extract.
FIG. 6(d) shows a study of optimal incubation time for efficient extraction of NSCs from SVZ of 6-hours with Ab-MNP's (2000 μg/ml in 5 μl of PBS) applied in vivo with corresponding images captured from the extract.
FIG. 6(e) shows a study of optimal incubation time for efficient extraction of NSCs from SVZ of 24-hours with Ab-MNP's (2000 μg/ml in 5 μl of PBS) applied in vivo with corresponding images captured from the extract.
Figure 7:
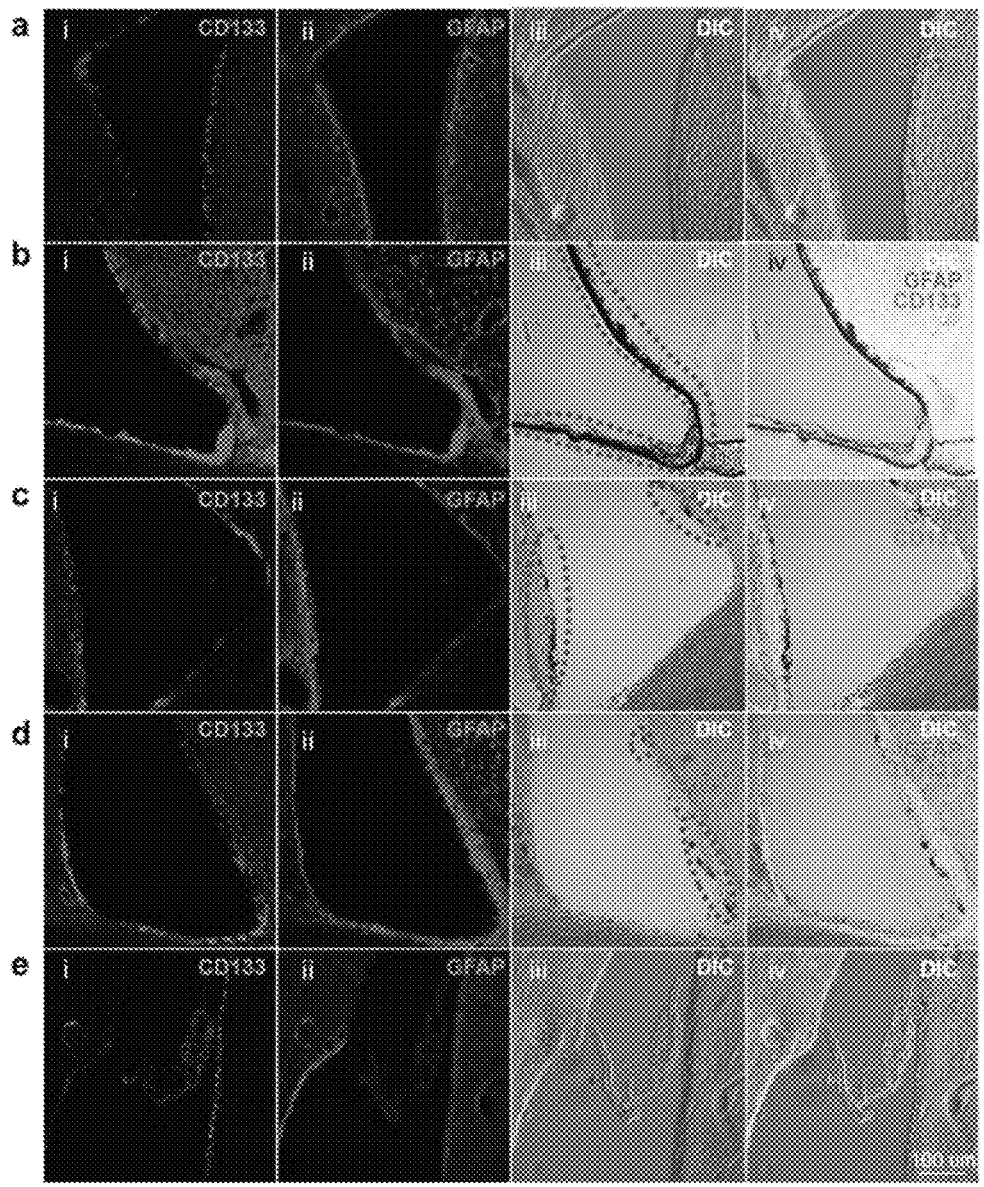
FIG. 7(a) shows the time events for 'magnetic agitation' without administration of Ab-MNPs.
FIG. 7(b) shows the time events for 0-min with corresponding images captured from the SVZ linings.
FIG. 7(c) shows the time events for 5-min with corresponding images captured from the SVZ linings.
FIG. 7(d) shows the time events for 10-min with corresponding images captured from the SVZ linings.
FIG. 7(e) shows the time events for 15-min with corresponding images captured from the SVZ linings.

An in vivo extraction of NSCs was then performed in the adult SD rats. The duration of incubation and magnetic agitation was found to be critical for an efficient extraction of NSCs from the SVZ region. Amongst different time points (0-hour, 1-hour, 3-hour, 6-hour and 24-hour), an extensive binding of the Ab-MNPs to the cells is observed at the 6-hour incubation time (FIGS. 6a-6e). It is envisaged that selective binding and removal of labels/cells from the endothelial linings of SVZ is rather dynamic in a rat body. An induction time was clearly required for the diffusion and binding process but a significant lower yield was obtained at the end of 24-hour incubation (FIG. 6d). The animals were also placed under a weak external spinning magnetic field generated by magnetic stirrer plate. As shown in FIGS. 7a-7e, 15 minutes of spinning was found to be the optimum time for the maximum detachment of the NSCs with no severe damage to the tissues. Interestingly, a high concentration of Ab-MNPs could be clearly observed on the lining of SVZ with 0 to 10 minute magnetic agitation. But the particle concentration on the lining was found progressively decreasing presumably due to their levitation and entering to the CSF fluid phase. In contrast, without the magnetic agitation the particle concentration on the lining was not much altered, implying that magnetic agitation is an essential step to liberate the surface assessable magnetic labelled cells into the fluid. Notice that the same animals were subject to this repeated magnetic surgery but all of them, after the treatments, were found alive and apparently healthy.

The In Situ Extraction and Isolation of NSCs

Figure 8:
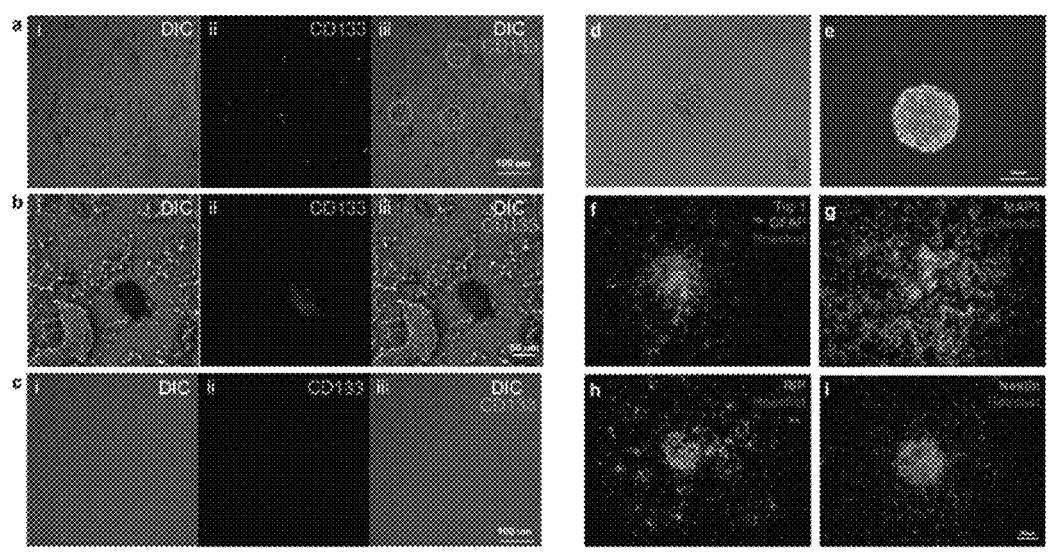
FIG. 8(a) shows the detached cells with CD133 immunoreactivity obtained after magnetic separation by a syringe.
FIG. 8(b) shows that Ab-MNP's bind specifically around the CD133 immunoreactive cells.
FIG. 8(c) shows when without magnetic agitation, $CD133^+$ cells are hardly found in the extract.
FIG. 8(d) shows an enlarged image of an isolated adult rat lateral ventricle $CD133^+$ cell forming a neurosphere before its differentiation into a different cell.
FIG. 8(e) shows $CD133^+$ cells generated neurospheres after 6 days in culture medium.
FIG. 8(f) shows $Tuj-1^+/MAP2^+$ neurons and $GFAP^+$ astrocytes 5 days after being plated onto a PDL-coated surface.
FIG. 8(g) shows $Tuj-1^+/MAP2^+$ neurons 5 days after being plated onto a PDL-coated surface.
FIG. 8(h) shows $RIP^+$ oligodendrocytes 5 days after being plated onto a PDL-coated surface.
FIG. 8(i) shows $nestin^+$ uncommitted progenitors 5 days after being plated onto a PDL-coated surface.
Figure 9:
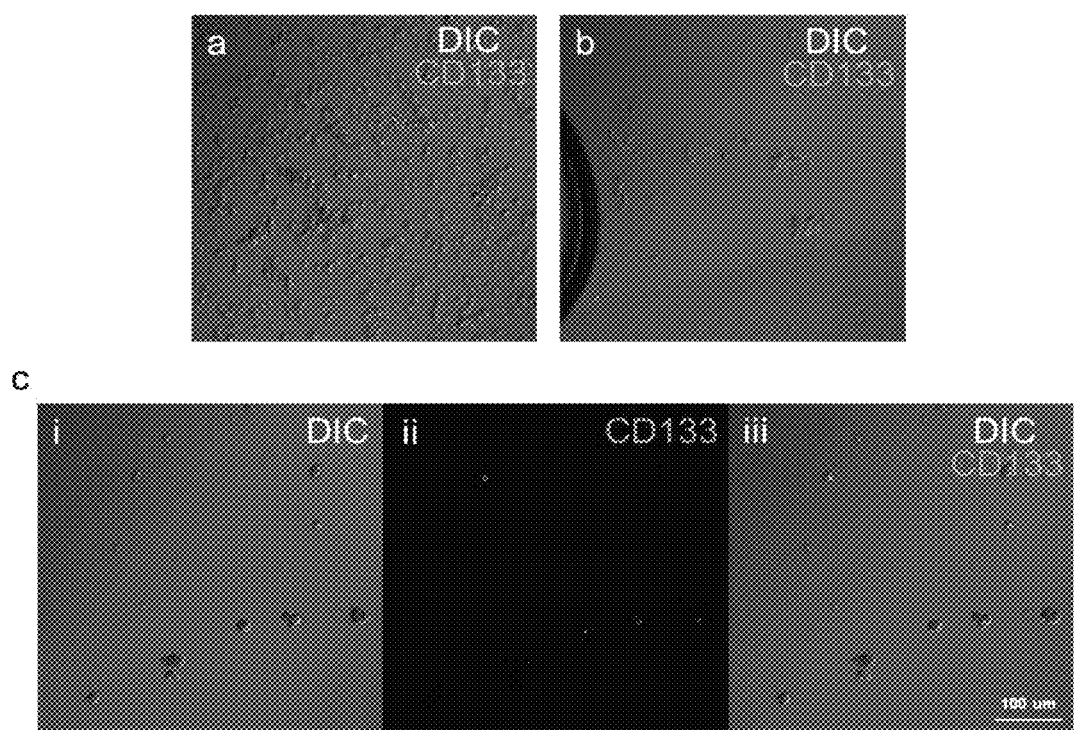
FIG. 9(a) shows the results where to increase the purity of the $CD133^+$ NSCs for the differentiation before application of a magnetic field.
FIG. 9(b) shows the results where to increase the purity of the $CD133^+$ NSCs for the differentiation after application of a magnetic field.
FIG. 9(c) shows the results where to increase the purity of the $CD133^+$ NSCs for the differentiation when a neodymium magnet probe was inserted into SVZ for in situ extraction of $CD133^+$ cells.

As a result, the 6-hour incubation time followed with 15-minute magnetic agitation was chosen as the treatment conditions for further experiments. The detached magnetically labeled cells were then extracted from the SVZ region by a micro-syringe (FIGS. 8a and 8b). The cells of interests (FIG. 8b) were isolated from the extracted cell mixture by magnetic means since the Ab-MNPs conjugated NSCs possess a magnetic separable property. Notably, the magnetic agitation was again proved to be essential for the detachment of the CD133$^+$ cells (FIG. 8c). The number of the CD133$^+$ cells for each extraction was around 221.67±79.89 cells/μl. After sorting by a conventional magnetic separation, CD133$^+$ NSCs were concentrated for further processing (FIG. 9). In addition, the magnetic CD133$^+$ cells could be also attracted by a neodymium magnetic probe which can be utilized as a tool for the selective cell extraction (FIG. 9c). Once the probe was inserted into SVZ of the subjects, the NSCs with the magnetic separable characteristics were quickly tagged on the probe. Consequently, the magnetic microsurgery process was found to be simple and safe to implement for the animal subjects.

Isolated Adult Rat Lateral Ventricular CD133$^+$ Cells Differentiating into Neural and Glial Lineages As shown in FIG. 8d, CD133 spheres were observed in adult rat CD133$^+$ cell culture 6 days after seeding (FIG. 8d) and their average diameter exceeds 100 μm at day 9 (FIG. 8e) whereas no neurosphere could be generated from the discarded extract (the remaining extract after the isolation of CD133$^+$ cells by magnetic separation). In this experiment, only cell clusters with diameter over 50 μm were counted as neurospheres. The sphere forming rate was ca. 4.49±2.02%. 5 days after differentiation induction, Tuj-1$^+$ and MAP2$^+$ neurones (FIGS. 8f and 8g), GFAP$^+$ astrocytes (FIG. 8f), RIP$^+$ oligodendrocytes (FIG. 8h) and nestin$^+$ uncommitted progenitors (FIG. 8i) were clearly observed, demonstrating the multipotency of the CD133$^+$ spheres. Thus, the in vitro proliferation and multipotent differentiation capability of the adult rat ventricular CD133$^+$ NSCs indicate that the magnetically extracted cells are active for use and modification.

Figure 10A:
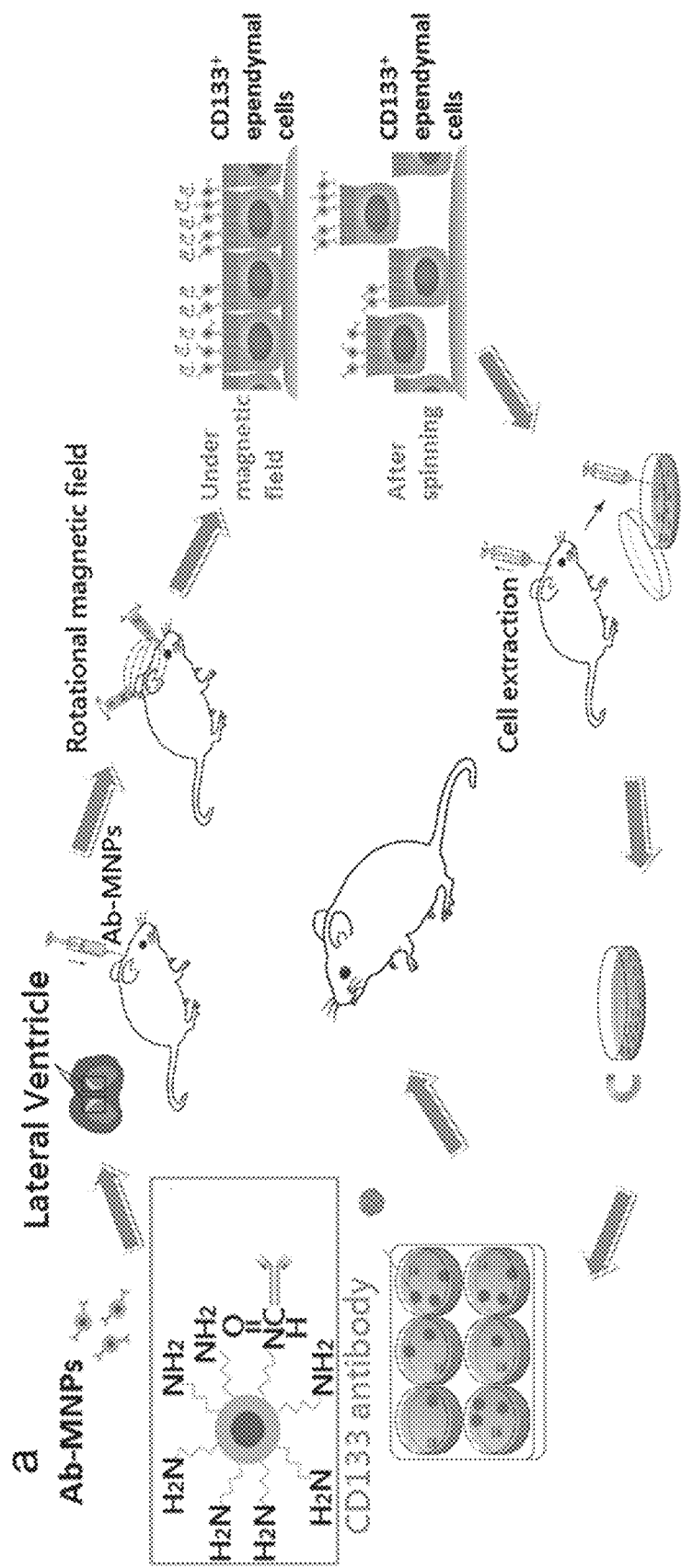
FIG. 10(a) shows a summary of the magnetic isolation of NSCs from brain tissue.
Figure 10B:
FIG. 10(b) shows the instrumentation used for the magnetic isolation.
Figure 10B:
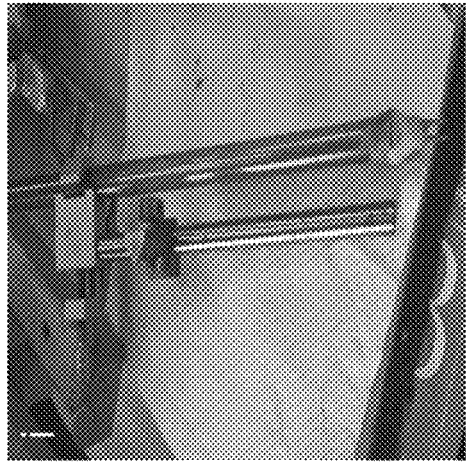

The New Magnetic Separable Technology for Extraction of Neural Stem Cells from Brain As a proof of concept, we have demonstrated an efficient method for a single-step isolation of active CD133$^+$ stem cells using magnetic means (FIG. 10), which have successfully generated neurospheres in vitro. Neurones, oligodendrocytes, astrocytes and nestin$^+$ uncommitted progenitors are also produced in further cells differentiations. Despite obtaining a relatively low extent of neurospheres (at present, ca. 4.49±2.02%) we believe that it is a first step to lead to the application of isolating multipotent neural stem cells/progenitor from adult brain without slaughtering the animal or inflicting significant damages. It is shown that the extracted adult rat ventricular zone CD133$^+$ NSCs can be proliferated quickly and generated neurospheres within 6 days of culture. The average diameter of the spheres of over 100 µm is observed on day 9. Upon induction of differentiation, the neural and glial cells are quickly emerging from the neurospheres, while the nestin$^+$ uncommitted progenitors are still largely available. This evidence clearly suggests that adult CD133$^+$ neural stem cells magnetically extracted particularly from surface linings of the lateral ventricle (LV) and SVZ with mild magnetic agitation are active and highly efficient in autologous stem cell based cell replacement therapy. Thus, the isolated stem cells/progenitors can be expanded in vitro rapidly and transplanted back for regenerative treatment.

From a practical point of view, magnetic extraction of ependymal cells as NSCs from the surface linings of LV and SVZ appears to be a safe operation and that a relative high concentration of the cells can also be obtained. These active extracted cells can be tailored-made or engineered in vitro to fit specific needs. MNPs shows low cytotoxicity and the amount needed for the extraction is generally very low (<0.19 mg/kg for the extraction of CD133$^+$ cells in SVZ; typically <4 mg/kg for contrast agents, as reported in J. S. Weinstein et al., *Superparamagnetic iron oxide nanoparticles: diagnostic magnetic resonance imaging and potential therapeutic applications in neurooncology and central nervous system inflammatory pathologies, a review. J Cerebr Blood F Met* 30, 15 (January, 2010)). Previous studies such as J. S. Weinstein et al., *Superparamagnetic iron oxide nanoparticles: diagnostic magnetic resonance imaging and potential therapeutic applications in neurooncology and central nervous system inflammatory pathologies, a review. J Cerebr Blood F Met* 30, 15 (January, 2010), L. Zecca, M. B. Youdim, P. Riederer, J. R. Connor, R. R. Crichton, *Iron, brain ageing and neurodegenerative disorders. Nat Rev Neurosci* 5, 863 (November, 2004) and K. R. Wagner, F. R. Sharp, T. D. Ardizzone, A. Lu, J. F. Clark, *Heme and iron metabolism: role in cerebral hemorrhage. Journal of cerebral blood flow and metabolism: official journal of the International Society of Cerebral Blood Flow and Metabolism* 23, 629 (June, 2003) also demonstrated that MNPs can be rapidly metabolized by the endothelial cells in blood-brain barrier, rendering the use of MNPs more acceptable for clinical practice. Thus, this technology though in an early stage of development, may give exciting potentials in biological and clinical applications, particularly in the area of regenerative medicinal treatment, from bench to bed.

Methodology

Synthesis of MNPs

MNPs were synthesized by Massart's method as described in L. L. Vatta, R. D. Sanderson, K. R. Koch, *Magnetic nanoparticles: Properties and potential applications. Pure Appl Chem* 78, 1793 (September, 2006) which based on the co-precipitation of iron (II) and iron (III) ion in 1:2 molar ratio. A solution of 4 ml 1 M iron (III) chloride (FeCl$_3$) and 1 ml 2 M iron (II) chloride (FeCl2) were added to 50 ml 0.7 M ammonium hydroxide (NH$_4$OH) with mechanical stirring. The solution was stirred for 1 hour until the black iron oxide nanoparticles were formed. The sediment was washed with distilled water twice under external magnetic field with the supernatant removed and dried overnight at 70° C.

Synthesis of FITC-APTES Ethanolic Solution

The pre-conjugated N-1-(3-trimethyloxy-silylpropyl)-N'-fluorsceyl thiourea (FITC-APTES) was prepared by adding 2.79 µl (3-Aminopropyl) triethoxysilane (APTES) to 1.11 µl 23 mM Fluorescein isothiocyanate (FITC) in ethanolic solutions and stirred in dark for 24 hours.

Preparation of Fluorescent Silica Coated MNPs

Silica coated MNPs were synthesized by water-in-oil (w/o) reverse micelle method as presented in C. W. Lu et al., *Bifunctional magnetic silica nanoparticles for highly efficient human stem cell labeling. Nano letters* 7, 149 (January, 2007). MNPs of 0.2846 g were dispersed in 1.7 ml distilled water and 8 ml n-hexanol. Then 38.5 ml cyclohexane and 9.4 ml Triton X-100 were added to the mixture under mechanical stirring to generate a microemulsion system. Then, 2 ml TEOS were added to the solution under stirring. After 6 hours, 5 ml 28% ammonium hydroxide were added into the mixture. After 24 hours, 1 ml FITC-APTES were added to the mixture and stirred in dark. After 24 hours, the FITC-silica coated MNPs were formed and isolated by external magnetic field. The particles were washed with distilled water and ethanol repeatedly and re-suspended in 5 ml distilled water.

Preparation of Fluorescent Silica Coated Ab-MNPs

The antibodies CD133 were covalently conjugated onto the silica coated magnetic nanoparticles by EDC/NHS chemistry in a manner as reported in Y. S. Lin, C. L. Haynes, *Synthesis and Characterization of Biocompatible and Size-Tunable Multifunctional Porous Silica Nanoparticles. Chem Mater* 21, 3979 (Sep. 8, 2009). Typically, 6.41 µl 15.6 µg/µl N-(3-Dimethylaminopropyl)-N-ethylcarbodiimide hydrochloride (EDC) and 4.16 µL 24 µg/µl N-Hydroxysuccinimide (NHS) were added to 2.24 mL 65.9 µg/µl fluorescent silica coated MNPs (160 µg). The mixture was incubated for 30 minutes. Consequently, 10 µl antibodies CD133 were added to the mixture and incubated for 1 hour in room temperature.

Transmission Electron Microscopy (TEM) and Data Analysis

MNPs solution of 5 µl was dropped on a carbon-coated copper grid (T200H-Cu, Electron Microscopy Science, Washington, USA) and dried in vacuum overnight. The TEM image of the dried sample was capture by a Technia G2 Transmission Electron Microscopy (FEI, USA) with an acceleration voltage of 200 kV, and a JEM 2100 TEM (JEOL, Japan) with an acceleration voltage of 210 kV for high solution TEM images respectively. The diameter of the MNPs was measured with the free domain software Image J (http://rsweb.nih.gov/ij/). A hundred nanoparticles were measured with the Freehand line and Measure function of the software. The distribution of the nanoparticles was fitted with the software OrginPro 8. The size of the nanoparticles was observed to be around 97 nm.

Isolation of Postnatal Day 0 Rat Forebrain CD133$^+$ Cells and CD133$^+$ Primary Astrocytes a. Isolation of Postnatal Day 0 Rat Forebrain CD133$^+$ Cells Walls of the lateral ventricles (forebrain CD133$^+$ cells) were dissected and digested in 0.25% trypsin (Biosera, UK) for 20 minutes at 37° C. Tissue after digestion was then triturated gently with the use of a flame-polished Pasteur pipette and filtered by using a 40 µm cell strainer (BD Falcon) to generate dissociated cells.

b. Isolation of CD133$^+$ Primary Astrocytes

The whole brain were dissected and digested in 0.25% trypsin (Biosera, UK) for 20 minutes at 37° C. after removing the meninges. Digested tissue was triturated gently with the use of a flame-polished Pasteur pipette and filtered by using a 70 µm cell strainer (BD Falcon). Vitamins and Ara C treatments were performed for the purification of astrocytes.

Lactate Dehydrogenase Cytotoxicity Assay

The cytotoxicity of the nanoparticles was indicated by the enzymatic activity of lactate dehydrogenase in postnatal day 0 rat SVZ cells [n=4]. The cells were treated with different concentrations of MNPs for 24 hours. The percentage of cells death was then measured by a commercial available cytotoxicity detection kit (LDH cytotoxicity kit, Roche Molecular Biochemicals) and spectrophotometer (Tecan Infinit F200) in the absorbance at 495 nm.

Nano Particle Based Purification of Postnatal Day 0 Rat Forebrain $CD133^+$ Cells and $CD133^+$ Astrocytes Dissociated cells from the lateral ventricle walls were incubated with Ab-MNPs for 1 hour at a concentration of 400 units/ml in plain DMEM-F12 medium (Life Technologies). The cells were then plated onto 6 well suspension culture plate (Greiner Bio-One) at a density of 25,000 cells/cm². Magnets were placed next to the wells to attract any MNP bound cells. After 30 minutes, medium was slowly drained from the away side of the well. Area close to the magnet was washed with plain DMEM-F12 medium for the recovery of the cells in solution. For flow cytometry analysis, nano-particle purified cells were fixed in 4% PFA for 10 minutes at 25° C. Fixed cells were then filtered through a 40 μm cell strainer (BD Falcon) and analyzed by BD FACSCanto II analyzer with 30,000 cells counted.

For immunocytochemistry, purified cells were attached onto microscope slides (Superforst, Thermo Scientific) by using cytospin and fixed in 4% paraformalaldehyde (PFA) for 10 minutes at 25° C. Fixed cells were then immunolabelled with CD133 primary antibody (1:10,000, mouse anti rat, Millipore) overnight at 4° C., followed by Alexa 488 secondary antibody (1:400, goat anti mouse, Life Technologies) for 30 minutes at 25° C. In the control experiment, mouse IgG1 isotype control (Life Technologies) was used to replace the CD133 primary antibody. Immunostained cells were viewed under epifluorescence microscope (Olympus IX71 inverted fluorescence microscope) and digital images were captured (Olympus DP71 camera with Olympus analysis LS Professional imaging software). The experiment was repeated for at least 3 times.

Animal Used

Adult Sprague-Dawley (SD) rats weighing 200-220 g were employed in the experiments. The animal experimental protocols performed in this study strictly confirmed and approved by the guidelines of the Animals (Control of Experiments) Ordinance, Department of Health, Hong Kong, the Committee on the Use of Human and Animal Subjects in Teaching and Research, Hong Kong Baptist University, and the Principles of Laboratory Animal Care (NIH publication no. 86-23, revised 1985). Both number and suffering of the animals were aimed to minimize in all procedures.

In Situ Extraction of NSCs in SVZ

Before the micro-surgery, the SD rats were first anesthetized with sodium pentobarbital (60 mg/kg; i.p.; Saggittal). A small midline sagittal skin incision was cut approximately 1 cm on the scalp to expose the skull. Two holes (Bregma: +0.05 cm, Medline: ±0.1 cm) with the diameter of 0.2 cm were stereotaxically drilled in the skull for the injection of Ab-MNPs into SVZ. The Ab-MNPs (5 μl, 2000 μg/ml) were then stereotaxically administrated into the target sites (Dura: −0.5 cm; 1 μl/min) and were allowed to incubate amongst different time points (O-hour [n=5], 1-hour [n=5], 3-hour [n=5], 6-hour [n=5] and 24-hour [n=5]). Before the extraction of NSCs, the spinning process (0 min [n=5], 5 min [n=5], min [n=5] and 15 min [n=5]) was performed in order to loosen the $CD133^+$ NSCs from single-layer multiciliated cells lining the ventricle system of the CNS. With the optimal duration of incubation and magnetic agitation, the NSCs (1 μl of extract; 0.5 μl/min) were then collected by a syringe for further culture [n=8]. The extraction of $CD133^+$ cells by the magnet probe was also demonstrated [n=3]. The probe was inserted into SVZ for 15 minutes to attract the cells of interest. The depth of the extraction was as same as the one of the injection (Dura: −0.5 cm). No nanoparticles were injected into SVZ of the controls [n=10].

In Vitro Propagation and Differentiation of Isolated Adult Rat Forebrain $CD133^+$ Cells Extracted $CD133^+$ cells were maintained in sphere forming medium (SFM) made up by DMEM-F12 medium supplemented with 20 ng/ml basic fibroblast growth factor (bFGF, Peprotech), 20 ng/ml epidermal growth factor (EGF, Peprotech) and B27 (Life Technologies). Cells were seeded at a clonal density of 10 cells per well in 96 well plate, which is modified from Coskun et al., 2008. Corning Ultra-Low attachment 96 well plates were used in this step. Supplements were added every 3 days and the cultures were maintained for 12 days. Spheres generated were collected for subsequent experiments.

To induce differentiation, spheres were plated onto poly-D-lysine (Sigma) coated 4 well plates (Nunc) and maintained in differentiation medium made up by Neurobasal medium (Life Technologies) supplemented with B27 (Life Technologies). The cells were maintained for 5 days in differentiation medium then fixed in 4% PFA for 10 minutes at 25° C. Fixed cells were then immunolabelled with the following primary antibodies: Tuj-1 (1:500, mouse anti rat, Convance), GFAP (1:400, rabbit anti rat, Dako), RIP (1:400, mouse anti rat, Hybridoma Bank) and Nestin (1:300, mouse anti rat, BD Phamingen) overnight at 4° C. Fixed cells were then immunolabelled with Alexa 488 (1:400, goat anti mouse, Life Technologies) and Alexa 594 (1:400, goat anti rabbit, Life Technologies) for 30 minutes at 25° C. Immunostained cells were viewed under epifluorescence microscope (Olympus IX71 inverted fluorescence microscope) and digital images were captured (Olympus DP71 camera with Olympus analysis LS Professional imaging software).

Perfusion

The rat was first deeply anesthetized with an overdose of sodium pentobarbital (60 mg/kg, i.p., Saggittal). It was then perfused transcardially with 250 ml of 0.9% saline to remove any blood followed by 250 ml fixative (3% paraformaldehyde with 0.1% glutaraldehyde solution in 0.1 M phosphate buffer (PB), pH 7.4) by using peristaltic pump. The perfusion flow rate was set to 25 ml/min for saline and 15 ml/min for fixative. The fixed brain was removed from the skull and stored overnight at 4° C. in post-fix solution (3% paraformaldehyde in 0.1 M PB, pH 7.4). The brain was rinsed three times with phosphate-buffered saline (PBS; 0.01 M, pH 7.4) and then cut into 70 μm sections by using vibratome. All the sections were collected in PBS at 4° C. before use. Immunofluorescence was performed to illustrate the immunoreactivity for CD133 and Glial fibrillary acidic protein (GFAP). Furthermore, the extracted cells were also mounted on clean slides with mounting medium (Dako) and covered with coverslips for the examination under the same parameters with laser scan confocal microscope (Olympus fluoview 1000).

Statistical Analysis

Mean±SD or SEM were indicated in the figures. Student's t-test was used to calculate the p-value between the experimental group and the control group. p-values <0.5 were considered significant The present invention discloses an in situ extraction method of neural stem cells in living subjects. Furthermore, this invention provides a means to develop tailor-made, in vivo, cell replacement therapy using individual subjects' own neural stem cells for transplantation and for treatment of neural related diseases. The method is envisaged for use in treating, preventing or delaying progression of a neural related disease of a patient, in particular, juvenile or adult human patients.

If desired, the different functions discussed herein may be performed in a different order and/or concurrently with each other. Furthermore, if desired, one or more of the above-described functions may be optional or may be combined.

Citation or identification of any reference in any other section of this application shall not be construed as an admission that such reference is available as prior art for the present application.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

The invention claimed is:

1. A method of extracting neural stem cells from a subject comprising:
   (a) introducing magnetic nanoparticles which can bind to neural stem cells into the subject such that
      the nanoparticles bind to neural stems cells forming nanoparticle-cell conjugates;
   (b) agitating the bound magnetic nanoparticle-cell conjugates by applying a moving magnetic field around the subjects skull, and
   (c) extracting the magnetic nanoparticle-cell conjugates with a magnetized extraction device.

2. The method according to claim 1, wherein the step of targeting further comprises a step of incubating the biological cells with the magnetic nanoparticles.

3. The method according to claim 1, wherein the magnetic force is applied external to the subject.

4. The method according to claim 1, wherein the magnetic nanoparticles are coated with silica.

5. The method according to claim 4, wherein the magnetic nanoparticles are surface conjugated with cell markers.

6. The method according to claim 1, wherein the magnetic nanoparticles are fluorescent.

7. The method according to claim 5, wherein the cell markers comprise stem cells surface markers.

8. The method according to claim 7, wherein the stem cells surface markers comprise antibodies CD133.

9. The method according to claim 1, wherein the biological cells are neural stem cells.

10. The method according to claim 1, wherein the method is performed at a subventricular zone of a brain of the subject.

11. The method according to claim 1, wherein the magnetic nanoparticles are superparamagnetic.

12. The method according to claim 1, wherein the magnetic nanoparticles are made from materials selected from a group consisting of iron oxide, maghemite ($Fe_2O_3$), magnetite ($Fe_3O_4$) nanoparticles, and a mixture thereof.

13. The method according to claim 1, wherein the step of introducing comprises a step of injecting.

14. The method according to claim 1, wherein the subject is a living organism.

15. The method according to claim 2, wherein the step of incubating lasts for less than or equal to about 24 hours.

16. The method according to claim 15, wherein the step of incubating lasts for about 6 hours.

17. The method according to claim 1, wherein the step of agitating lasts for less than or equal to about 15 min.

18. The method according to claim 1, wherein the step of extracting comprises using of tools selected from the group of a syringe, a magnet probe, a neodymium magnet and a mixture thereof.

19. The method according to claim 1, wherein the method is applied in vivo.

20. The method according to claim 1, wherein the method is used for treating, preventing or delaying progression of a neural related disease of a patient.

21. The method according to claim 20, wherein the patient comprises juvenile or adult human.

* * * * *